United States Patent [19]
Restifo et al.

[11] Patent Number: 5,846,540
[45] Date of Patent: Dec. 8, 1998

[54] IMMUNOGENIC CHIMERAS COMPRISING NUCLEIC ACID SEQUENCES ENCODING ENDOPLASMIC RETICULUM SIGNAL SEQUENCE PEPTIDES AND AT LEAST ONE OTHER PEPTIDE, AND THEIR USES IN VACCINES AND DISEASE TREATMENTS

[75] Inventors: Nicholas P. Restifo, Washington, D.C.; Steven A. Rosenberg, Bethesda, Md.; Jack R. Bennink, Olney, Md.; Igor Bacik, Rockville, Md.; Jonathan W. Yewdell, Silver Springs, Md.

[73] Assignee: The United States of America as represented by the Department of Health and Human Services, Washington, D.C.

[21] Appl. No.: 471,341

[22] Filed: Jun. 6, 1995

Related U.S. Application Data

[63] Continuation of Ser. No. 32,902, Mar. 17, 1993, abandoned.

[51] Int. Cl.⁶ .......................... A61K 39/00; A61K 39/02; C12N 15/63; C07H 21/04
[52] U.S. Cl. ................................. 424/192.1; 424/234.1; 424/265.1; 424/277.1; 435/320.1; 536/23.4; 536/24.1
[58] Field of Search ............................. 424/184.1, 192.1, 424/199.1, 234.1, 265.1, 277.1; 435/69.1, 172.3, 320.1; 514/44; 536/22.1, 23.1, 23.4, 24.1; 935/32, 57

[56] References Cited

FOREIGN PATENT DOCUMENTS

| | | |
|---|---|---|
| 0207165 | 1/1987 | European Pat. Off. . |
| 0356409 | 2/1990 | European Pat. Off. . |
| WO 94/04171 | 3/1994 | WIPO . |
| WO 94/04557 | 3/1994 | WIPO . |

OTHER PUBLICATIONS

Rouse et al. (1988) Antiviral cytotoxic T lymphocyte induction and vaccination. Rev. Infect. Dis. 10:16–33, Jan. 1988.
B. Moss (1991) Science 252:1662–1667.
F. D. Ledley (1991) Human Gene Therary 2:77–83.
G. Von Heijne (1985) J. Mol. Biol. 184:99–105.
A. Knuth et al. (1991) Current Opinion in Immunology 3:659–664.
S.–L. Hu et al (1988) J. Virology 62(1):176–180.
M. Polydefkis et al (1990) J. Exp. Med. 171:875–887.
W. Koch et al (1983) J. Virology 45(1):1–9.
B. Lethé et al. (1992) Eur. J. Immunology 22:2283–2288.
Eisenlohr, L.C. et al., (1992) *Cell* 71:963–972.
Eisenlohr, L.C. et al., (1992) *J. Exp. Med.* 175: 481–487.
Anderson, K. et al., (1991) *J. Exp. Med.*, 174:489–492.
Trowsdale, et al., (1990) *Nature*, 348:741–744.
Monaco, J.S., et al., (1990) *Science* 250:1723–1726.
Townsend, A.R.M., et al., (1984) *Cell* 39:13–25.
Deverson, E., et al., (1990) *Nature*, 748:738–741.
Spies, T., et al., (1990) *Nature*, 348:744–747.
Yewdell, J.W., et al., (1988) *Science* 239:637–640.
Bennink, J.P., et al., (1982) *Nature* 296:75–76.
Yewdell, J.W., et al., (1985) *Proc. Natl. Acad. Sci. USA*, vol. 82, pp. 1785–1789.

*Primary Examiner*—David Guzo
*Assistant Examiner*—Robert Schwartzman
*Attorney, Agent, or Firm*—Morgan & Finnegan, L.L.P.

[57] ABSTRACT

Immunogenic chimeric proteins comprising an endoplasmic reticulum signal sequence and at least one other peptide are disclosed. The invention relates to the design of vaccinia virus constructs capable of directing host organism synthesis of immunogenic chimeric proteins which can be used as immunogens, as vaccines, or in methods of treatment for cancer, infectious diseases, or autoimmune diseases.

24 Claims, 7 Drawing Sheets

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 17 amino acid residues
        ( B ) TYPE: amino acid
        ( C ) STRANDEDNESS: unknown
        ( D ) TOPOLOGY: unknown ( x i ) SEQUENCE DESCRIPTION: SEQ ID NO:1:

Met Arg Tyr Met Ile Leu Gly Leu Leu Ala Leu Ala Ala Val
1               5                   10

Cys Ser Ala
15

( 2 ) INFORMATION FOR SEQ ID NO:2:

( i ) SEQUENCE CHARACTERISTICS:
        ( A ) LENGTH: 10 amino acid residues
        ( B ) TYPE: amino acid
        ( C ) STRANDEDNESS: unknown
        ( D ) TOPOLOGY: unknown ( x i ) SEQUENCE DESCRIPTION: SEQ ID NO:2:

Ser Gly Pro Ser Asn Thr Pro Pro Glu Ile
1               5                   10

( 2 ) INFORMATION FOR SEQ ID NO:3:

( i ) SEQUENCE CHARACTERISTICS:
        ( A ) LENGTH: 9 amino acid residues
        ( B ) TYPE: amino acid
        ( C ) STRANDEDNESS: unknown
        ( D ) TOPOLOGY: unknown ( x i ) SEQUENCE DESCRIPTION: SEQ ID NO:3:

Ser Glu Phe Leu Leu Glu Lys Arg Ile
1               5

( 2 ) INFORMATION FOR SEQ ID NO:4:

( i ) SEQUENCE CHARACTERISTICS:
        ( A ) LENGTH: 9 amino acid residues
        ( B ) TYPE: amino acid
        ( C ) STRANDEDNESS: unknown
        ( D ) TOPOLOGY: unknown ( x i ) SEQUENCE DESCRIPTION: SEQ ID NO:4:

Phe Leu Arg Gly Arg Ala Tyr Gly Ile
1               5

( 2 ) INFORMATION FOR SEQ ID NO:5:

( i ) SEQUENCE CHARACTERISTICS:
        ( A ) LENGTH: 9 amino acid residues
        ( B ) TYPE: amino acid (C) STRANDEDNESS: unknown
(D) TOPOLOGY: unknown (xi) SEQUENCE DESCRIPTION: SEQ ID NO:5:

Thr Tyr Gln Arg Thr Arg Ala Leu Val
1               5

(2) INFORMATION FOR SEQ ID NO:6:

(i) SEQUENCE CHARACTERISTICS:
(A) LENGTH: 9 amino acid residues
(B) TYPE: amino acid
(C) STRANDEDNESS: unkown
(D) TOPOLOGY: unknown (xi) SEQUENCE DESCRIPTION: SEQ ID NO:6:

Leu Pro Tyr Leu Gly Trp Leu Val Phe
1               5

(2) INFORMATION FOR SEQ ID NO:7:

(i) SEQUENCE CHARACTERISTICS:
(A) LENGTH: 27 amino acid residues
(B) TYPE: amino acid
(C) STRANDEDNESS: unknown
(D) TOPOLOGY: unknown (xi) SEQUENCE DESCRIPTION: SEQ ID NO:7:

Met Arg Tyr Met Ile Leu Gly Leu Leu Ala Leu Ala Ala Val
1               5                   10

Cys Ser Ala Ala Leu Pro Tyr Leu Gly Trp Leu Val Phe
15                  20                  25

(2) INFORMATION FOR SEQ ID NO:8:

(i) SEQUENCE CHARACTERISTICS:
(A) LENGTH: 90 base pairs
(B) TYPE: nucleic acid
(C) STRANDEDNESS: single
(D) TOPOLOGY: linear (xi) SEQUENCE DESCRIPTION: SEQ ID NO:8:

ACCACCATGT ACATGATTTT AGGCTTGCTC GCCCTTGCGG                          4

CAGTCTGCAG CGCGGCCCTG CCTTATCTAG GGTGGCTGGT                          8

CTTCTGATAG                                                          9

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:9:

AGTCGACGAT CGCGGCCGCT                                               20

(2) INFORMATION FOR SEQ ID NO:10:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:10:

```
AGCGGCCGCG ATCGTCGACT                                                            20
```

(2) INFORMATION FOR SEQ ID NO:11:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:11:

```
TCGACCACCA TGAGGTACAT GATTTTAGGC TTGCTCGCCC                                      40
TTGCGGCAGT CTGCAGCGCG GCCGCCGCCA A                                               71
```

(2) INFORMATION FOR SEQ ID NO:12:

(i) SEQUENCE CHARACTERISTICS:
        (A) LENGTH: 71 base pairs
        (B) TYPE: nucleic acid
        (C) STRANDEDNESS: single
        (D) TOPOLOGY: linear (xi) SEQUENCE DESCRIPTION: SEQ ID NO:12:

```
GGCCTTGGCG GCCGCCGCGC TGCAGACTGC CGCAAGGGCG                                      40
AGCAAGCCTA AAATCATGTA CCTCATGGTG G                                               71
```

(2) INFORMATION FOR SEQ ID NO:13:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:13:

```
GGCCACGTAC CAGCGGACGC GGGCCCTGGT GTGATAGGTA                                      40
CC                                                                               42
```

(2) INFORMATION FOR SEQ ID NO:14:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:14:

```
CTTGGGTACC TATCACACCA GGGCCCGCGT CCGCTGGTAC                                      40
GT                                                                               42
```

IMMUNOGENIC CHIMERAS COMPRISING NUCLEIC ACID SEQUENCES ENCODING ENDOPLASMIC RETICULUM SIGNAL SEQUENCE PEPTIDES AND AT LEAST ONE OTHER PEPTIDE, AND THEIR USES IN VACCINES AND DISEASE TREATMENTS

This is a continuation of application Ser. No. 08/032,902, filed on Mar. 17, 1993, now abandoned.

FIELD OF INVENTION

The present invention is in the field of immunotherapy. More specifically, the invention relates to use in vivo of immunogenic chimeric proteins comprising an endoplasmic reticulum signal peptide and at least one other peptide as immunogens in vaccines and in methods of treatment for cancer, viral infections, bacterial infections, parasitic infections or autoimmune diseases in mammals.

BACKGROUND OF INVENTION

The establishment of immunotherapies based on thymus—derived lymphocytes (T cells) as a treatment modality for cancer and other diseases in humans is an area of considerable research interest (Oethgen, H. F. et al. (1991) in Biologic Therapy of Cancer: eds.: DeVita, V. T. Jr., Hellman, S., Rosenberg, S. A. J. B. Lippincott, p. 87). A major hindrance to the development of effective T cell-based immunotherapies is that antigen presentation on the surface of cells is often inadequate to elicit a T cell response to the antigen. Thus, a major aim of researchers in fields such as cancer biology, virology and immunology is the development of methods which enhance the presentation of antigens to T cells. In order to better understand the present invention, a brief review of how T cells recognize, or fail to recognize, antigens is presented below (see also Restifo, N.P Biologic Therapy of Cancer Updates 2:1–10 (1992); Yewdell, J. W. Adv. in Immunology 52:1–123(1992)).

Unlike B cells which can recognize antigens not presented in the context of other molecules, T cells can only recognize antigens in the context of a major histocompatibility complex (MHC) on the surface of a target cell. In particular, two types of MHC molecules exist and each type, noncovalently linked with antigenic peptides, constitutes a ligand for different subsets of T cells. More specifically, class I MHC/peptide complexes are recognized by $CD8^+$ T cells while class II MHC/peptide complexes are recognized by $CD4^+$ T cells. Of interest to researchers involved in the development of T cell based immunotherapies, $CD8^+$ T cells, sometimes termed cytotoxic T lymphocytes or CTLs, have been demonstrated to be capable of directly killing target cells presenting a class I/peptide complex on their cell surface and of secreting cytokines which may signal for the destruction of these target cells. These properties of $CD8^+T$ cells have stimulated numerous investigators to focus on the study of the processes leading to the formation of class I/peptide complexes within target cells and the subsequent presentation of these complexes on the surface of the target cells in order to better understand the molecular apparati involved in the presentation of peptides to $CD8^+T$ cells. To date, although the processes involved in the cleavage and transport of peptides that are bound by class I MHC molecules are only now being characterized, some details are known.

In brief, the generation of antigenic peptides for class I molecules from cytosolic proteins (Tevethia, S. S., et al. Virology 107:13–23 (1980); Bennink, J. R., et al. Nature 296:75–76 (1982); Yewdell, J. W., et al. Proc. Natl. Acad. Sci. USA 82:1785–1789 (1985); Yewdell, J. W., et al. Science 239:637–640 (1988); Townsend, A. R. M., et al. Cell 39, 13–25 (1984)) is achieved by unknown cytosolic proteases. Once formed in the cytosol, these peptides are then delivered to the endoplasmic reticulum (ER) via a process which requires the presence of two MHC encoded gene products termed TAP 1 and TAP 2 (Deverson, E., et al. Nature 348:738–741 (1990); Trowsdale, J., et al. 348:741–744 (1990); Spies, T., et al. Nature 348:744–747 (1990); Monaco, J. J., et al. Science 250:1723–1726 (1990)). In the ER, the peptides associate noncovalently with class I MHC molecules to form a class I MHC/peptide complex which is then transported to the cell surface. The class I/peptide complex presented on the cell surface is now capable of serving as a ligand for cell surface receptors on $CD8^+$ T cells and hence, of eliciting a T cell response against the presented peptide. Due to the complexity of the processing pathways which ultimately results in antigen presentation to $CD8^+$ T cells, deficiencies in expression of any of the components of the antigen processing pathways outlined above might be expected to result in reduced presentation of antigen to CTLs.

Recent studies by both Eisenlohr et al. (Cell 71:963–972 (1992)) and Anderson et al (J. Exp. Med. 174:489–492 (1991)) have demonstrated that although presentation of antigens to CTLs is dramatically reduced in a cell line having deletions in the genes encoding TAP 1 and TAP 2 relative to that observed in control cells, efficient antigen presentation in a TAP-deficient cell line could be achieved via transfection of these cells with "minigenes" in which the antigenic peptide was placed immediately carboxy-terminal to an ER signal sequence. Such signal sequences are generally found at the $NH_2$— terminus of proteins and their function is to target such proteins to the ER membrane. It should be noted however that the enhancing effect of the ER signal sequence on antigen presentation observed in these studies was not noted in control cells and was therefore, only observed in in vitro transfection or infection of a TAP-deficient cell line. However, evidence supporting the idea that the presentation of antigens processed from the cytosol might be limiting in vivo was recently provided by the observation by other investigators that TAP 1 and TAP 2 expression is enhanced following exposure of cells to gamma—interferon (Trowsdale, J., et al. Cell, 348:741–744 (1990). This result suggested that TAP-mediated peptide delivery can be limiting in vivo as well as in vitro and that therefore, methods which could enhance the transport of peptides in vivo, or bypass transport activity entirely, might result in enhanced presentation of peptides to T cells.

SUMMARY OF INVENTION

The present invention includes immunogenic chimeric proteins comprising an endoplasmic reticulum signal sequence peptide and at least one other peptide. Immunogenic chimeric proteins are used in vivo to elicit specific T cell response.

The invention relates to synthetic nucleic acid sequence capable of directing production of immunogenic chimeric protein as well as equivalent natural nucleic acid sequences. For the purposes of this application, nucleic acid sequence refers to RNA, DNA, cDNA or any synthetic variant thereof which encodes immunogenic chimeric protein.

The invention also relates to a vaccine for immunizing a mammal against cancer, viral infection, bacterial infection, parasitic infection or autoimmune disease comprising an immunogenic chimeric protein or a nucleic acid sequence encoding said immunogenic chimeric protein in a pharmaceutically acceptable carrier.

The invention also provides pharmaceutical compositions for the prevention or treatment of mammals afflicted with cancer, viral infection, bacterial infection, parasitic infection or autoimmune disease where said pharmaceutical compositions comprise immunogenic chimeric protein or nucleic acid sequence encoding said immunogenic chimeric protein in a suitable diluent or carrier.

The invention further relates to a method for treating cancer, viral infection, bacterial infection, parasitic infection or autoimmune disease comprising:
(a) immunizing mammals with an amount of immunogenic chimeric protein or nucleic acid sequence encoding said immunogenic chimeric protein, said amount effective to elicit a specific T cell response;
(b) isolating said T cells from said immunized mammals; and
(c) administering said T cells to said immunized mammal or to an unimmunized mammal in a therapeutically effective amount.

DETAILED DESCRIPTION OF INVENTION

Figure 1:
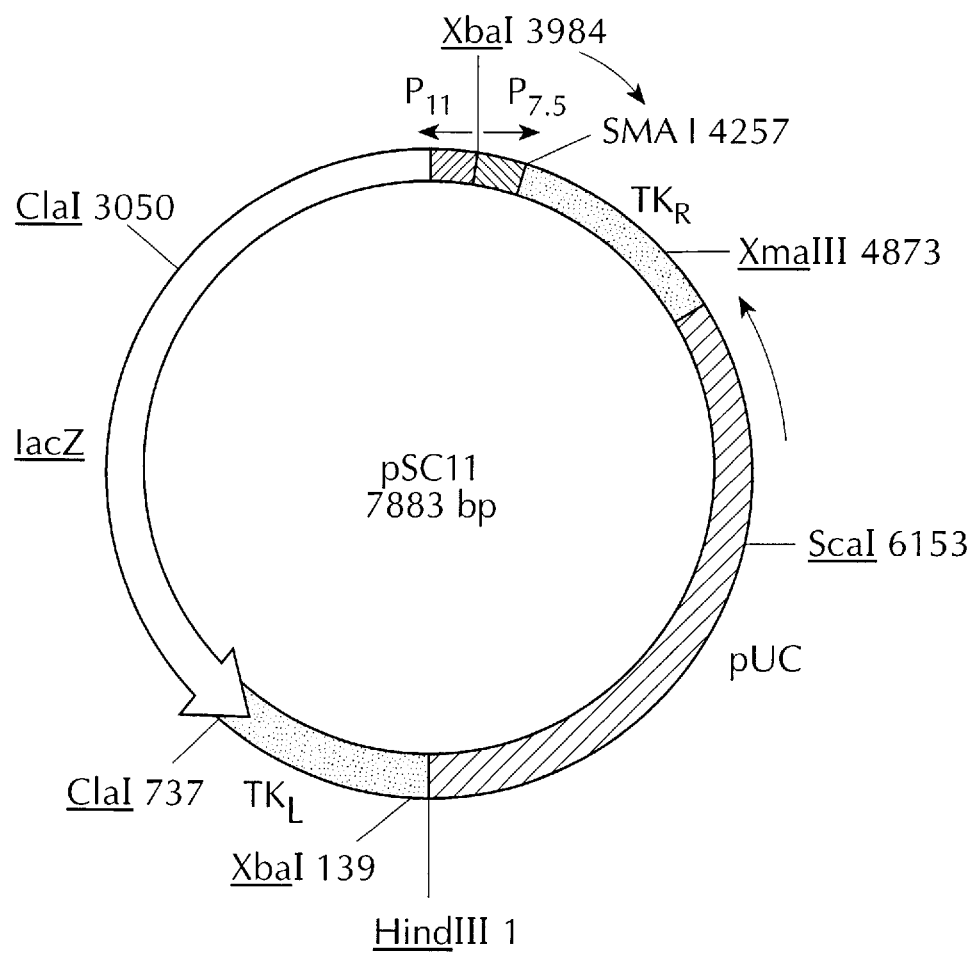
FIG. 1 shows the construction of the vaccinia virus (VV) construct used to express immunogenic chimeric protein comprising the adenoviral E3/19K signal sequence peptide and another peptide of choice.

The present invention relates to immunogenic chimeric proteins comprising an endoplasmic reticulum (ER) signal sequence peptide and at least one other peptide. For the purposes of the present invention, "signal sequence peptide" refers to amino acid sequences of about 15 to about 25 amino acids in length which are known in the art to be generally located at the amino terminus of proteins and which are capable of targeting said proteins to the endoplasmic reticulum. In a preferred embodiment, the signal sequence peptide used is derived from the adenovirus type 5, E3/19 K gene product (Persson, H. et al Proc. Natl. Acad Sci. USA 77:6349–6353 (1980)) and is shown as SEQ ID NO: 1

Met Arg Tyr Met Ile Leu Gly Leu Leu Ala Leu Ala Ala Val Lys Ser Ala

However, those skilled in the art would readily appreciate that many other signal sequence peptides are known (van Heijne, G., J. Mol. Biol. 184:99–105 (1985)) and that these peptide sequences or analogues thereof can be substituted for SEQ ID NO:1 in the immunogenic chimeric protein of the present invention.

By "other peptide", as used throughout the specification and the claims, denotes that a peptide is immunogenic when used as part of an immunogenic chimeric protein containing an ER signal sequence peptide; the "other peptide" by itself may or may not be immunogenic. In one embodiment, the other peptide can range from about 5 to about 1000 amino acids in length and may be derived from a tumor cell, virus, bacteria, or parasite, or it may be associated with an autoimmune disease.

In a preferred embodiment, the other peptide is about 8 to 10 amino acids in length. Examples of such peptides include, but are not limited to, tumor peptides, such as the adenovirus E1A peptide (Kast et al. Cell, 59:603–614 (1989)) shown as SEQ ID NO: 2

Ser Gly Pro Ser Asn Thr Pro Pro Glu Ile;

the SV40 T antigen peptide (Gould et al. J. Virol., 65:5401–5409 (1991)) shown as SEQ ID NO: 3

Ser Glu Phe Leu Leu Glu Lys Arg Ile;

and viral peptides such as the Epstein Barr virus antigen peptide (Burrows, S. R. et al. Eur J. Immunol. 22:191–195 (1992)) shown as SEQ ID NO: 4

Phe Leu Arg Gly Arg Ala Tyr Gly Ile;

and influenza virus A/PR/8/34 nucleoprotein peptide NP 147–153 (Rotzscke, O. et al. Nature 348:252–254 (1990)) shown as SEQ ID NO: 5

Thr Tyr Gln Arg Thr Arg Ala Leu Val.

The exemplary tumor peptide is P1A derived from P815 mastocytoma cells (Lethe, B., Eur J. Immunol., 22:2283–2288 (1992)). The P1A sequence is shown as SEQ ID NO: 6

Leu Pro Tyr Leu Gly Trp Leu Val Phe.

In the present invention, the order in which the signal sequence peptide and other peptide are arranged within the immunogenic chimeric protein can be varied. In one embodiment, the other peptide precedes, or is amino-terminal to, the signal sequence peptide. In a preferred embodiment, the signal sequence peptide is amino terminal to the other peptide. Regardless of the order in which they are arranged, the signal sequence peptide and the other peptide may be separated by zero to about 1000 amino acids. In a preferred embodiment, the signal sequence peptide and the other peptide are directly adjacent to each other, i.e. separated by zero amino acids.

In yet another embodiment, multiple copies of the other peptide may be contained within an immunogenic chimeric protein. The number of copies of said other peptide can range from 2 to about 100. A preferred number of copies is from about 2 to about 10. In a preferred embodiment, the signal sequence peptide is amino terminal to the multiple copies of the other peptide and these multiple copies are arranged in a continuous uninterrupted manner.

In a further embodiment, several different other peptides can be contained in an immunogenic chimeric protein with the number of different other peptides ranging from two to about ten. In a preferred embodiment, these other peptides are preceded by a signal sequence peptide and are arranged in a continuous, uninterrupted manner with the order in which the other peptides are arranged being variable.

Immunogenic chimeric proteins of the present invention may be provided as a synthetic polypeptide or as a protein synthesized from a nucleic acid sequence encoding the immunogenic chimeric protein.

In one embodiment, a synthetic immunogenic chimeric protein may be synthesized based on the known amino acid sequences of the signal sequence peptide and the other peptide which are to be contained within the immunogenic chimeric protein. The amino acid sequence of a preferred immunogenic chimeric protein comprising ER signal sequence amino terminal to the P1A tumor peptide is shown as SEQ ID NO 7:

Met Arg Tyr Met Ile Leu Gly Leu Leu Ala Leu Ala Ala Val Lys
Ser Ala Ala Leu Pro Tyr Leu Gly Trp Leu Val Phe

Those skilled in the art would be aware that immunogenic chimeric proteins ranging from about 25 to about 100 amino acids in length can be synthesized by automated instruments sold by a variety of manufacturers or they can be custom ordered and prepared.

In another embodiment, immunogenic chimeric protein can be expressed from nucleic acid sequences where such sequences can be DNA, cDNA, RNA or any variant thereof which is capable of directing protein synthesis. In one embodiment, restriction digest fragments containing a coding sequence for a signal sequence peptide and the other peptide respectively, can be ligated together and inserted into a suitable expression vector that functions in prokaryotic or eukaryotic cells. Such restriction digest fragments may be obtained from clones isolated from prokaryotic or eukaryotic sources which encode either signal sequence peptide or the other peptide.

By suitable expression vector is meant a vector that is capable of carrying and expressing a complete nucleic acid sequence coding for immunogenic chimeric protein.

Such vectors include any vectors into which a nucleic acid sequence as described above can be inserted, along with any preferred or required operational elements, and which vector can then be subsequently transferred into a host organism and replicated in such organism. Preferred vectors are those whose restriction sites have been well documented and which contain the operational elements preferred or required for transcription of the nucleic acid sequence.

The "operational elements" as discussed herein include at least one promoter, at least one operator, at least one leader sequence, at least one determinant, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence.

To construct the cloning vector of the present invention, it should additionally be noted that multiple copies of the nucleic acid sequence encoding immunogenic chimeric protein and its attendant operational elements may be inserted into each vector. In such an embodiment, the host organism would produce greater amounts per vector of the desired immunogenic chimeric protein. In a similar fashion, multiple different immunogenic chimeric proteins may be expressed from a single vector by inserting into the vector a copy (or copies) of nucleic acid sequence encoding each immunogenic chimeric protein and its attendant operational elements. In yet another embodiment, a polycistronic vector in which multiple immunogenic chimeric proteins (either identical in sequence or different) may be expressed from a single vector is created by placing expression of each immunogenic chimeric protein under the control of an internal ribosomal entry site (IRES) (Molla A. et al Nature 356:255–257 (1992); Jang S. K. et al J. of Virol. 263:1651–1660(1989)). The number of multiple copies of the DNA sequence encoding immunogenic chimeric protein which may be inserted into the vector is limited only the ability of the resultant vector due to its size, to be transferred into and replicated and transcribed in an appropriate host organism.

Preferred expression vectors are those that function in a eukaryotic cell. Examples of such vectors include but are not limited to vaccinia virus, adenovirus or herpes viruses. Most preferred vectors are vaccinia viruses. Example 1 describes the construction of vaccinia virus construct, VV-ESNP147–155, used in the present invention.

In yet another embodiment, a synthetic oligonucleotide encoding ER chimeric protein may be synthesized and subcloned into a suitable expression vector. A preferred oligonucleotide sequence is shown as SEQ ID NO: 8:

ACC ACC ATG TAC ATG ATT TTA GGC TTG CTC GCC CTT GCG GCA
GTC TGC AGC GCG GCC CTG CCT TAT CTA GGG TGG CTG GTC TTC
TGA TAG

Those skilled in the art would readily appreciate that oligonucleotides can be synthesized by automated instruments sold by a variety of manufacturers or they can be customer ordered and prepared.

Once a nucleic acid sequence encoding immunogenic chimeric protein is present in a suitable expression vector, the expression vector may then be used for purposes of expressing the immunogenic chimeric protein in a suitable eukaryotic cell system. Such eukaryotic cell systems include but are not limited to cell lines such as HeLa, L929, T2 or RMA-S. Preferred eukaryotic cell systems are T2 and RMA-S. One preferred method involves use of vaccinia virus constructs to transfect T2 or RMA-S cell lines. The expressed immunogenic chimeric protein may be detected by methods known in the art such as metabolic radiolabelling.

In a further embodiment, the immunogenic chimeric protein expressed by the cells can be obtained as crude lysate or it can be purified by standard protein purification procedures known in the art which may include differential precipitation, molecular sieve chromatography, ion-exchange chromatography, isoelectric focusing, gel electrophoresis, affinity, and immunoaffinity chromatography and the like. In the case of immunoaffinity chromatography, the immunogenic chimeric protein may be purified by passage through a column containing a resin which has bound thereto antibodies specific for the immunogenic chimeric protein.

The present invention also provides a method of immunization comprising administering an amount of the immunogenic chimeric protein effective to elicit a T cell response to the other peptide. Such T cell response can be measured by a variety of assays including $^{51}$Cr release assays (Restifo, N. P. J of Exp. Med., 177:265–272(1993)). The T cells capable of producing such a cytotoxic response may be $CD8^+$ T cells ($CTL_s$), $CD4^+$ T cells or both.

The immunogenic chimeric protein can be administered in a pure or substantially pure form but it is preferable to present it as a pharmaceutical composition, formulation or preparation. Such formulation comprises an immunogenic chimeric protein together with one or more pharmaceutically acceptable carriers and optionally other therapeutic ingredients. The formulations may conveniently be presented in unit dosage form and may be prepared by an method well-known in the pharmaceutical art.

All the methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product into the desired formulation.

Formulations suitable for intravenous, intramuscular, subcutaneous, or intraperitoneal administration conveniently comprises sterile aqueous solutions of the active ingredient with solutions which are preferably isotonic with the blood of the recipient. Such formulations may be conveniently prepared by dissolving solid active ingredient in water containing physiologically compatible substances such as sodium chloride (e.g. 0.1–2.0M), glycine, and the like, and having a buffered pH compatible with physiological conditions to produce an aqueous solutions, and rendering said solution sterile. These may be present in unit or multi-dose containers, for example, sealed ampoules or vials.

The formulations of the present invention may incorporate a stabilizer. Illustrative stabilizers are polyethylene glycol, proteins, saccharide, amino acids, inorganic acids, and organic acids which may be used either on their own or as admixtures. These stabilizers are preferably incorporated in an amount of 0.11–10,000 parts by weight per part by weight of antibody. If two or more stabilizers are used in aqueous solutions at the appropriate concentration and pH. The specific osmotic pressure does such aqueous solution is generally in the range of 0.1–3.0 osmoses, preferably in the range of 0.80–1.2. The pH of the aqueous solution is adjusted to be within the range of 5.0–9.0, preferably within the range of 6–8. In formulating the immunogenic chimeric protein of the present invention, anti-adsorption agent may be used.

Additional pharmaceutical methods may be employed to control the duration of action. Controlled release preparations may be achieved through the use of polymer to complex or absorb the proteins or their derivatives. The controlled delivery may be exercised by selecting appropriate macromolecules (for example polyester, polyamine acids, polyvinyl, pyrrolidone, ethylenevinylacetate, methylcellulose, carboxymethylcellulose, or protamine sulfate) and the concentration of macromolecules as well as the methods of incorporation in order to control release. Another possible method to control the duration of action by controlled-release preparations is to incorporate the proteins, protein analogs, or their functional derivatives, into particles of a polymeric material such as polyesters, polyamine acids, hydrogels, poly(lactic acid) or ethylene vinylacetate copolymers.

Alternatively, instead of incorporating these agents into polymeric particles, it is possible to entrap these materials in microcapsules prepared, for example, by coacervation techniques or by interfacial polymerization, for example, hydroxymethylcellulose or gelatin-microcapsules and poly (methylmethacylate) microcapsules, respectively, or in colloidal drug delivery systems, for example, liposomes, albumin microspheres, microemulsions, nanoparticles, and nanocapsules or in macroemulsions.

When oral preparations are desired, the compositions may be combined with typical carriers, such as lactose, sucrose, starch, talc magnesium stearate, crystalline cellulose, methyl cellulose, carboxymethyl cellulose, glycerin, sodium alginate or gum arabic among others.

In yet another embodiment, the method of immunization may comprise administering a nucleic acid sequence capable of directing host organism synthesis of immunogenic chimeric protein in an amount effective to elicit a T cell response. Such nucleic acid sequence may be inserted into a suitable expression vector by methods known to those skilled in the art (FIG. 1). Expression vectors suitable for producing high efficiency gene transfer in vivo include retroviral, adenoviral and vaccinia viral vectors. Operational elements of such expression vector are disclosed previously in the present specification and are known to one skilled in the art. A preferred vector is vaccinia virus. An expression vector containing nucleic acid sequence capable of directing host cell synthesis of immunogenic chimeric protein can be administered in a pure or substantially pure form or as a complex with a substance having affinity for nucleic acid and an internalizing factor bound to the substance having affinity for nucleic acid. (Wu G. et al. J. Biol. Chem 262:4429–4432 (1987); Wagner E. et al. Proc. Natl. Acad Sci. USA 87:3655–3659 (1990)). A preferred substance having affinity for nucleic acid is a polycation such as polylysine. Internalizing factors include ligands having specificity for receptors present on the surface of immunogen presenting cells such as macrophages, lymphocytes, B cells, dendritic cells or Langerhans cells. Preferred internalizing factors include but are not limited to transferrin and antibodies specific to immunogen presenting cells.

Expression vectors containing a nucleic acid sequence encoding immunogenic chimeric protein can be administered intravenously, intramuscularly, subcutaneously, intraperitoneally or orally. A preferred route of administration is intravenously.

The immunogenic chimeric proteins and expression vectors containing nucleic acid sequence capable of directing host organism synthesis of immunogenic chimeric proteins may be supplied in the form of a kit, alone, or in the form of a pharmaceutical composition as described above.

The present invention also relates to a vaccine for immunizing a mammal against cancer, viral infection, bacterial infection, parasitic infection, or autoimmune disease, comprising an immunogenic chimeric protein or an expression vector containing nucleic acid sequence capable of directing host organism synthesis of immunogenic chimeric protein in a pharmaceutically acceptable carrier. In an alternative embodiment, multiple expression vectors, each containing nucleic acid sequence capable of directing host organism synthesis of a different immunogenic chimeric proteins, may be administered as a polyvalent vaccine.

Vaccination can be conducted by conventional methods. For example, an immunogenic chimeric protein can be used in a suitable diluent such as saline or water, or complete or incomplete adjuvants. Further, the immunogenic chimeric protein may or may not be bound to a carrier to make the protein more immunogenic. Examples of such carrier molecules include but are not limited to bovine serum albumin (BSA), keyhole limpet hemocyanin (KLH), tetanus toxoid, and the like. The immunogenic chimeric protein can be administered by any route appropriate for eliciting T cell response such as intravenous, intraperitoneal, intramuscular, subcutaneous, and the like. The immunogenic chimeric protein may be administered once or at periodic intervals until a T cell response is elicited. Doses of immunogenic chimeric protein effective to elicit a T cell response range from about 0.00001 to about 10 mg/kg. Doses of immunogenic chimeric protein-encoding expression vector effective to elicit a T cell response range from about $10^5$ to about $10^7$ plaque forming units. T cell response may be detected by a variety of methods known to those skilled in the art, including but not limited to, cytotoxicity assay, proliferation assay and cytokine release assays.

The present invention also includes a method for treating cancer, viral infection, bacterial infection, parasitic infection or autoimmune disease, comprising administering pharmaceutical compositions comprising an immunogenic chimeric protein or an expression vector containing nucleic acid sequence capable of directing host organism synthesis of an immunogenic chimeric protein in a therapeutically effective amount. Again as with vaccines, multiple expression vectors may also be administered simultaneously. When provided therapeutically, the immunogenic chimeric protein or immunogenic chimeric protein-encoding expression vector is provided at (or shortly after) the onset of the infection or at the onset of any symptom of infection or disease caused by, cancer, virus, bacteria, parasites or autoimmune disease. The therapeutic administration of the immunogenic chimeric protein or immunogenic chimeric protein-encoding expression vector serves to attenuate the infection or disease.

A preferred embodiment is a method of treatment comprising administering a vaccinia virus containing nucleic acid sequence encoding immunogenic chimeric protein to a mammal in therapeutically effective amount. Since vaccinia virus vectors capable of directing host organism synthesis of immunogenic chimeric protein containing tumor peptide or viral peptide have already been demonstrated to be capable of eliciting a T cell responses against these peptides (see Examples 2–5), its utility in treating disease is indicated.

The present invention also includes a method for treating cancer, viral infection, bacterial infection, parasitic infection, or autoimmune disease, comprising:

(a) immunizing mammals with an amount of immunogenic chimeric protein or an expression vector capable of directing host organism synthesis of immunogenic chimeric protein effective to elicit a specific T cell response;

(b) isolating said T cells from said immunized mammal; and (c) administering said T cells to said immunized mammal or to an unimmunized mammal in a therapeutically effective amount.

T cells populations reactive against the other peptide (e.g. tumor peptide) contained in an immunogenic chimeric protein may be isolated from a peripheral blood sample or spleen cells of a donor immunized with the immunogenic chimeric protein from about 3 to about 30 days after immunization. Epstein-Barr virus (EBV) can be used to immortalize human lymphocytes or a human fusion partner can be used to produce human-human hybridomas. Primary in vitro immunization with immunogenic chimeric protein can also be used in the generation of T cells reactive to the immunogenic peptide.

T cells are cultured for about 7 to about 90 days (Yanelli, J. R. J. Immunol. Methods 139:1–16 (1991)) and then screened to determine the clones of the desired reactivity against the other peptide contained in the immunogenic chimeric protein using known methods of assaying T cell reactivity; T cells producing the desired reactivity are thus selected.

The above described T cells may be used for in vivo use as treatment for individuals afflicted with cancer, viral infection, bacterial infection, parasitic infection or autoimmune diseases by administering from about $10^7$ to about $10^{11}$ T cells to a mammal intravenously, intraperitoneally, intramuscularly or subcutaneously. Preferred routes of administration are intravenously or intraperitoneally.

Any articles or patents referenced herein are incorporated by reference. The following examples illustrate various aspects of the invention but are in no way intended to limit the scope thereof.

MATERIAL AND METHODS

The materials and methods used in the following examples were as follows:

Methods. The vaccinia virus (VV) constructs used in the following examples are as follows: VV-NP codes for the full-length nucleoprotein (NP) gene of the influenza virus A/Puerto Rico/8/34 (PR8) (Yewdell, J. W. et al. Proc. Natl. Acad. Sci U.S.A. 82:1785–1789 (1985); VV-NP 147–155 codes for the nine amino acid "minimal determinant" of the NP gene (Rötzschke, O. et al Nature 348:252–254 (1990)); VV-ES NP147–155 uses the nine amino acid long "minimal determinant" from the NP gene of PR8 but is preceded by the ER signal sequence from adenovirus type 5 E3/19K; VV-NP147–155 ES in which the ER signal sequence is placed downstream from the minimal determinant; VV-ES OVA 257–264 which consists of the same ER signal sequence but followed by the minimal determinant of ovalbumin; VV-ES VSV 52–59 which consists of the same ER signal sequence but followed by the minimal determinant from the nucleoprotein gene of vesicular stomatitis virus (VSV) (Van Bleek et al Nature 348:213–215 (1990) and VV-ESP1A which consists of the same ER signal sequence but followed by the P1A tumor antigen (Lethé, B., EwJ.

Immunol., 22:2283–2288 (1992)). The construction of vaccinia virus constructs encoding NP, ES NP147–155, and NP147–155 have been described (Yewdell, J. W. et al (1985); Eisenlohr, L. C. et al (1992); and Wei M. L. et al (1992)). VV-ES OVA 257–264 was constructed as described for VV-ES NP147–155 with the exception that a double stranded synthetic oligonucleotide corresponding to the OVA 257–264 peptide (Carbone, F. R. et al. J. Exp. Med. 169:603–610 (1989)) was inserted into the plasmid immediately downstream of the nucleotides encoding the E3/19K leader sequence with an additional Ala codon. To construct VV-NP147–155 ES, a double stranded oligonucleotide corresponding to the E3/19K ER signal sequence modified to encode a NdeI site at its 5' coding end and double stop codons at the 3' coding end was inserted into the SalI and NotI sites of modified pSC11 (Eisenlohr et al (1992)). This intermediate plasmid (pSC11-ES) was then digested with SalI and NdeI, and ligated with a double stranded oligonucleotide encoding the appropriate overhangs, an initiating Met, and residues corresponding to NP 147–155. VV-ES VSV 52–59 and VV-ESP1A were constructed following the protocol outlined in Example 1. Foreign genes were inserted into the VV thymidine kinase (TK) gene by homologous recombination in CV-1 cells (Chakrabarti, S. et al Mol. Cell-Biol. 5:3403–3409 (1985)), and after three rounds of 3 plaque purification in the TK⁻ human 143B osteosarcoma cell line (American Type Culture Collection or ATCC) in the presence of bromodeoxyuridine, were grown in the same cells. VV-NP was produced using a plasmid that lacks the β-galactosidase reporter gene (used to identify rVVs (recombinant vaccinia viruses) with plasmid inserts after homologous recombination).

$^{51}$Cr RELEASE ASSAY FOR T CELL ACTIVITY

Eight to 10 week old female BALB/c mice were injected intravenously (i.v.) with 5×10⁶ plaque-forming units (PFU) rVVs. Six days later, spleens were removed and dispersed to single cell suspensions in Iscove's modified DMEM (IDMEM) medium with 7.5% fetal bovine serum (FBS) (Biofluids, Rockville, Md.) using a Dounce homogenizer. The target cells used to assay for cytotoxicity of the splenocyte T cells were P815 mastocytoma cells, (American Type Culture Collection or ATCC)), CT26 fibrosarcoma cells, or RMA-S tumor cells (Ljungren, H. G. et al. J. Exp. Med. 162:1745–1759 (1985)). Target cells were sensitized for lysis by antigen-specific CD8⁺ T cells by coincubating target cells for 1 h at 37° C. with Na$^{51}$CrO$_4$ and with 1 μM of the peptides indicated in the appropriate Examples. HPLC-purified peptides NP 147–155, OVA 257–264, VSV 52–59 and P1A were provided by the Biological Resources Branch, NIAID, Bethesda, Md. In Examples 2–4, P815 cells were infected at a multiplicity of 10 PFU/cell with wild-type VV for one hour prior to labelling for 1 hour at 37° C. with Na$^{51}$CrO$_4$ ($^{51}$Cr) (Restifo, N. P. (1993)). Target cells (either pulsed with the appropriate peptide or infected with vaccinia virus) were incubated with splenocytes for 6 hours at 37° C. at various effector to target ratios (E:T) (see Examples for specific ratios). The amount of released $^{51}$Cr was determined by gamma-counting and the percent specific lysis was calculated as follows: [(experimental cpm−spontaneous cpm)/(maximal cpm−spontaneous cpm)]×100.

EXAMPLE 1

Construction of a Vaccinia Virus Construct Used to Express An Immunogenic Chimeric Protein The plasmid pSC11 (a gift of Dr. Bernard Moss, NIAID, Bethesda, Md.) shown in FIG. 1, was the starting material for construction of a plasmid containing nucleic acid sequence encoding an immunogenic chimeric protein which can be inserted into vaccinia virus via homologous recombination (Chakrabarti et al., 1985). This example describes a protocol for the production of a plasmid containing a nucleic acid sequence encoding immunogenic chimeric protein ESNP147–155, but this protocol could be readily utilized to produce plasmids encoding other immunogenic chimeric proteins. Complementary oligonucleotides shown as SEQ ID NO: 9:

AGT CGA CGA TCG CGG CCG CT and SEQ ID NO: 10:

AGC GGC CGC GAT CGT CGA CT were synthesized, (Surgery Branch, National Cancer Institute, Bethesda, Md.) kinased and annealed together to form a double stranded DNA polylinker containing Sal I and Not I restriction sites. This polylinker DNA was then inserted into Sma I-digested pSC11 by blunt end ligation to create a pSC11 plasmid with Sal I and Not I polylinker plasmid (pSC11 linker plasmid). Complementary oligonucleotides shown as SEQ ID NO: 11:

TCG ACC ACC ATG AGG TAC ATG ATT TTA GGC TTG CTC GCC CTT GCG GCA GTC TGC AGC GCG GCC GCC GCC AA and SEQ ID NO: 12:

GGC CTT GGC GGC CGC CGC GCT GCA GAC TGC CGC AAG GGC GAG CAA GCC TAA AAT CAT GTA CCT CAT GGT GG were synthesized, kinased and annealed together to form a double-stranded DNA encoding the adenoviral E3/19K signal sequence plus Not I and Sty I restriction sites. This E3/19K signal sequence DNA was then subcloned into the aforementioned pSC11 linker plasmid cleaved with Sal I and Not I to create a plasmid designated E3/19K signal plasmid. Complementary oligonucleotides shown as SEQ ID NO: 13

SEQ ID NO: 13:
GGC CAC GTA CCA GCG GAC GCG GCC CCT GGT GTG ATA GGT ACC and SEQ ID NO: 14:
CTT GGG TAC CTA TCA CAC CAG GGC CCG CGT CCG CTG GTA CGT were synthesized, kinased, and annealed together to form a double-stranded DNA sequence encoding the NP147–155 peptide plus double stop codons and Not I and Sty I restriction sites. The NP147–155 DNA was then subcloned into the E3/19K signal plasmid cleaved with Not I and Sal I. The resultant plasmid encoded ESNP147–155 and was inserted into vaccinia virus as described to produce the vaccinia virus construct VV-ESNP147–155.

EXAMPLE 2

Efficacy of Vaccinia Virus Construct VV-ES NP 147–155 in Generation of a T Cell Response To test the idea that the efficiency of antigen presentation might be optimized by the use of an immunogenic chimeric protein comprising a peptide preceded by an ER signal sequence, $5\times10^6$ plaque forming units (pfu) of one of the above-described vaccinia virus constructs: VV-NP, VV-ES NP 147–155, VV-NP 147–155 ES, or VV-ES OVA 257–264 were intravenously administered to mice.

Six days following intravenous injection, mice were sacrificed and their spleens were harvested. Splenocytes were tested in a $^{51}$CR-release assay for cytotoxicity against P815 target cells alone (left panels), P815 cells pulsed with synthetic peptide corresponding to NP (influenza virus nucleoprotein) amino acid residues 147–155 (middle panel) or P815 cells infected with vaccinia virus (right panels). The splenocytes (i.e. the effector cells) derived from the immunized mice were incubated at varying ratios as indicated on the horizontal (x) axis of FIG. 2 with a constant number of P815 target cells. The cytotoxicity of the splenocytes towards the $^{51}$Cr-labelled target cells was measured as the % specific $^{51}$Cr release as shown on the y axis. As expected, all of the vaccinia virus constructs tested showed a similar ability to elicit a CD8$^+$ T cell response toward vaccinia virus infected P815 cells (right panel) and a similar inability to elicit a CD8$^+$ T cell response against control uninfected P815 cells (left panel). However, only splenocytes derived from mice immunized with VV-ES NP147–155 demonstrated NP specific activity (middle panel) as shown by their ability to lyse P815 target cells preincubated with a synthetic peptide corresponding to NP residues 147–155. In addition, only splenocytes derived from mice immunized with VV-ES NP 147–155 were observed to specifically lyse influenza virus infected P815 cells (data not shown) at levels roughly similar to those observed with peptide NP 147–155 pulsed P815 cells (middle panel, FIG. 2). Moreover, the inability of splenocytes derived from mice immunized with VV-ES OVA 257–264 to specifically lyse peptide NP 147–155-pulsed cells (middle panel) indicated that the enhanced immunogenicity of VV-ES NP147–155 cannot be attributed to non-specific effects of the E3/19K signal sequence. Finally, the large difference between the cytotoxic activity of splenocytes derived from mice immunized with either VV-ES NP147–155 or VV-NP147–155 ES toward peptide NP 147–155-pulsed P815 cells (middle panel) indicated that the E3/19K signal sequence did not act solely by increasing the hydrophobicity of the peptide.

EXAMPLE 3

Figure 3A:
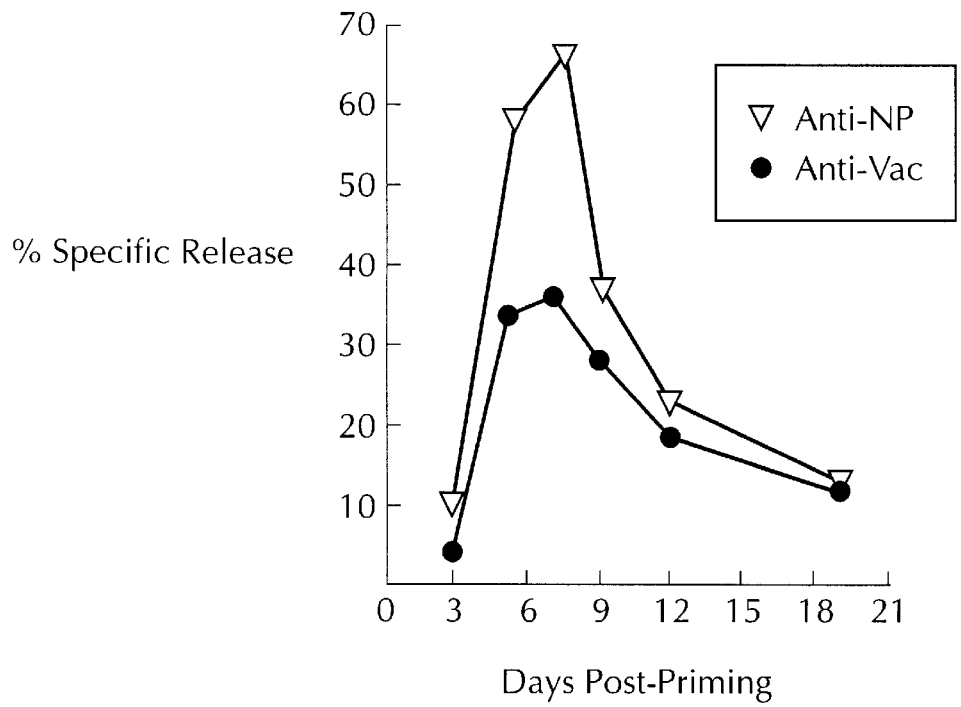
FIGS. 3A and 3B show the results of $^{51}$Cr release assays in which splenocytes derived from mice immunized sequentially (to allow CD8$^+$ T cell activity to be measured in a single assay) with vaccinia virus VV-ESNP 147–155 (FIG. 3A) or VV-NP (FIG. 3B) were incubated at various effector:target (E:T) ratios with P815 target cells pulsed with synthetic peptide NP 147–155 (open triangles) or with P815 cells infected with wild type -VV (closed circles).
Figure 3B:
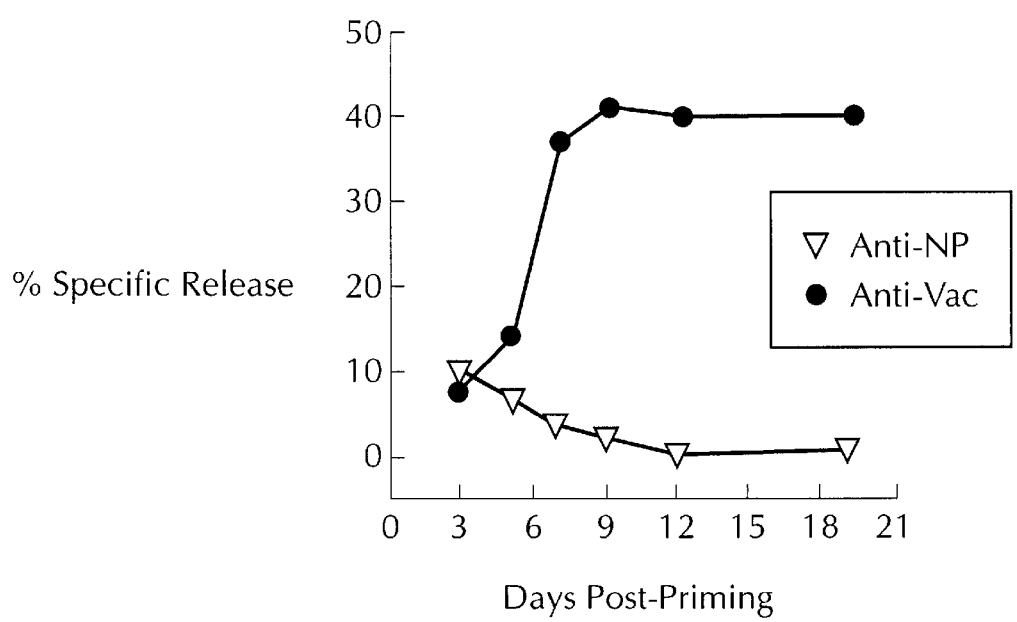

Kinetics of Response of Splenocytes Derived From Mice Immunized With Vaccinia Virus Constructs To examine the possibility that the apparently enhanced immunogenicity of VV-ES NP147–155 relative to other VV constructs is due to a difference in the kinetics of the CD8$^+$ T cell response, mice were injected with $5\times10^6$ pfu of VV-ES NP147–155 (FIG. 3A) or VV-NP (FIG. 3B) and their splenocytes tested for NP-specific CD8$^+$ T cell activity between 1 and 19 d later using peptide-pulsed P815 (peptide NP147–155) target cells. The effector to target ratio used was 200:1. Peak NP peptide-specific activity (i.e. P815 cells pulsed with NP147–155 peptide designated by open triangles) was observed with splenocytes obtained from mice between 5 and 9 days following immunization with VV-ES NP147–155. This NP-specific activity paralleled peak VV-specific activity (closed circles, P815 cells infected with vaccinia virus). Splenocytes from VV-NP immunized mice exhibited negligible NP-specific lytic activity over the entire course of the experiment. This result was not due to the inability of this vaccinia virus construct to elicit a CD8$^+$ T cell response, since a VV-specific response of similar magnitude to that elicited by VV-ES NP147–155 was observed.

EXAMPLE 4

Figure 4:
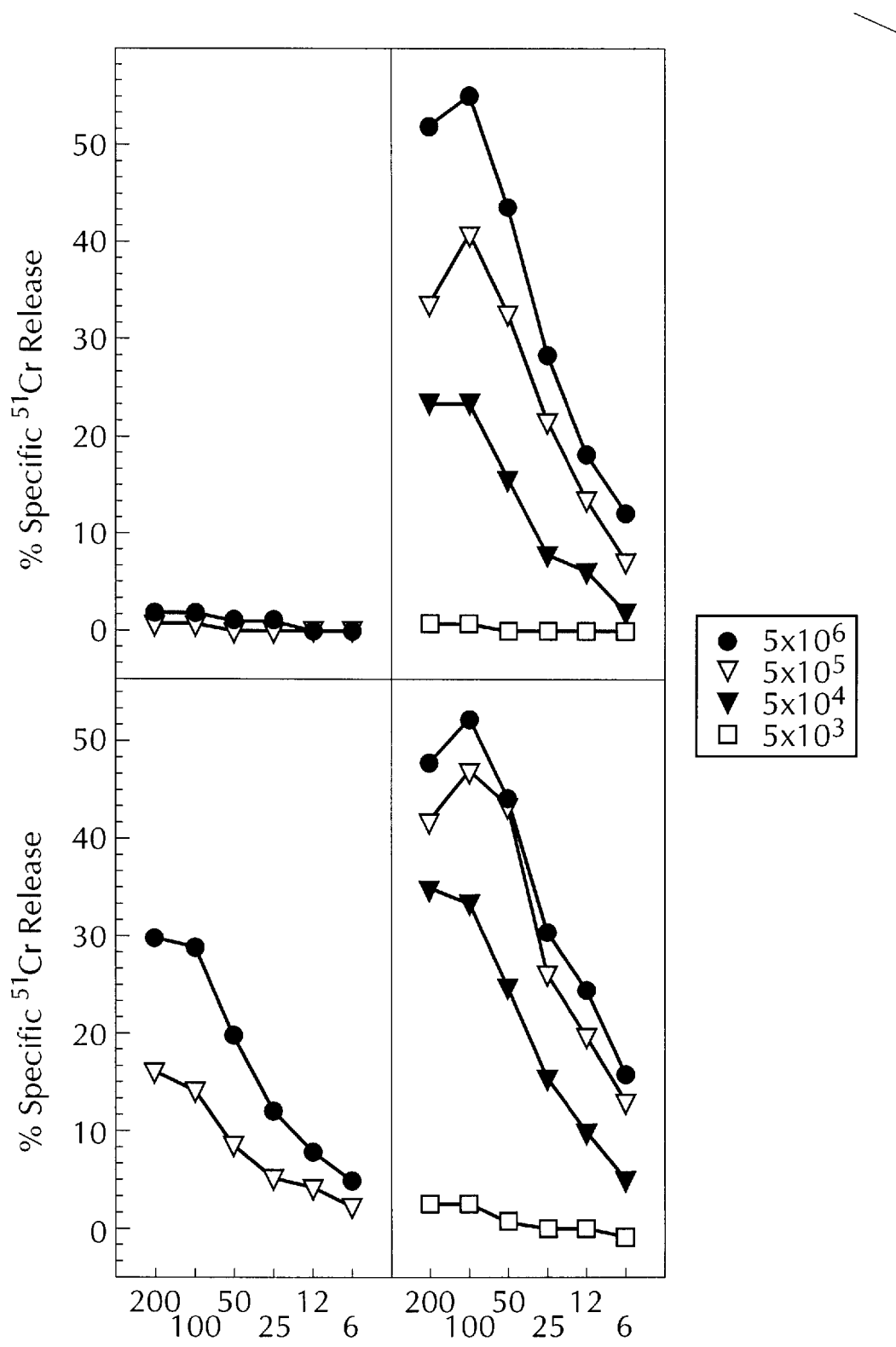
FIG. 4 shows the results of $^{51}$Cr release assays in which splenocytes derived from mice immunized with varying doses of vaccinia virus VV-NP (left panels), or VV-ESNP 147–155 (right panels) were incubated at various effector:target (E:T) ratios with P815 cells infected with VV-NP (top panels) or with wild type -VV (bottom panels).

CD8$^+$ T Cell Response Elicited in Mice Immunized With Varying Doses of Vaccinia Virus Constructs The primary CD8$^+$ T cell response of mice to increasing doses of VV constructs was compared (FIG. 4; doses given are indicated by the symbols to the right of the figure) (top panels use P815 target cells pulsed with peptide NP147–155 and bottom panels use P815 target cells infected with vaccinia virus). Mice were sacrificed and their spleens were harvested six days following immunization. The results of the $^{51}$Cr release assays show that while mice failed to mount a significant NP-specific response following injection with $5\times10^6$ pfu of VV-NP (left panels) or VV-NP147–155 (middle panels) (injection with greater amounts of virus resulted in significant death of the mice), immunization with $5\times10^4$ pfu of VV-ES NP147–155 (right panels) induced an easily detectable NP-specific CD8$^+$ T cell response. The effector to target ratios assayed are shown at the bottom of the figure. Thus, VV-ES NP147–155 is at least 100 fold more efficient at inducing a primary NP-specific CD8$^{++}$ cell response than the other VV constructs. The anti-VV CD8$^+$ T cell response (bottom panels, P815 target cells infected with vaccinia virus) was examined at each dose of vaccinia virus constructed tested. The results shown in the bottom panels confirmed that all of the VV constructs were able to induce comparable responses, and thus, that the differences in immunogenicity are related to the residues flanking the NP determinant (i.e. the ES signal sequence).

EXAMPLE 5

Efficacy of Vaccinia Virus Construct VV-ESP1A in Generating a T Cell Response

Figure 2:
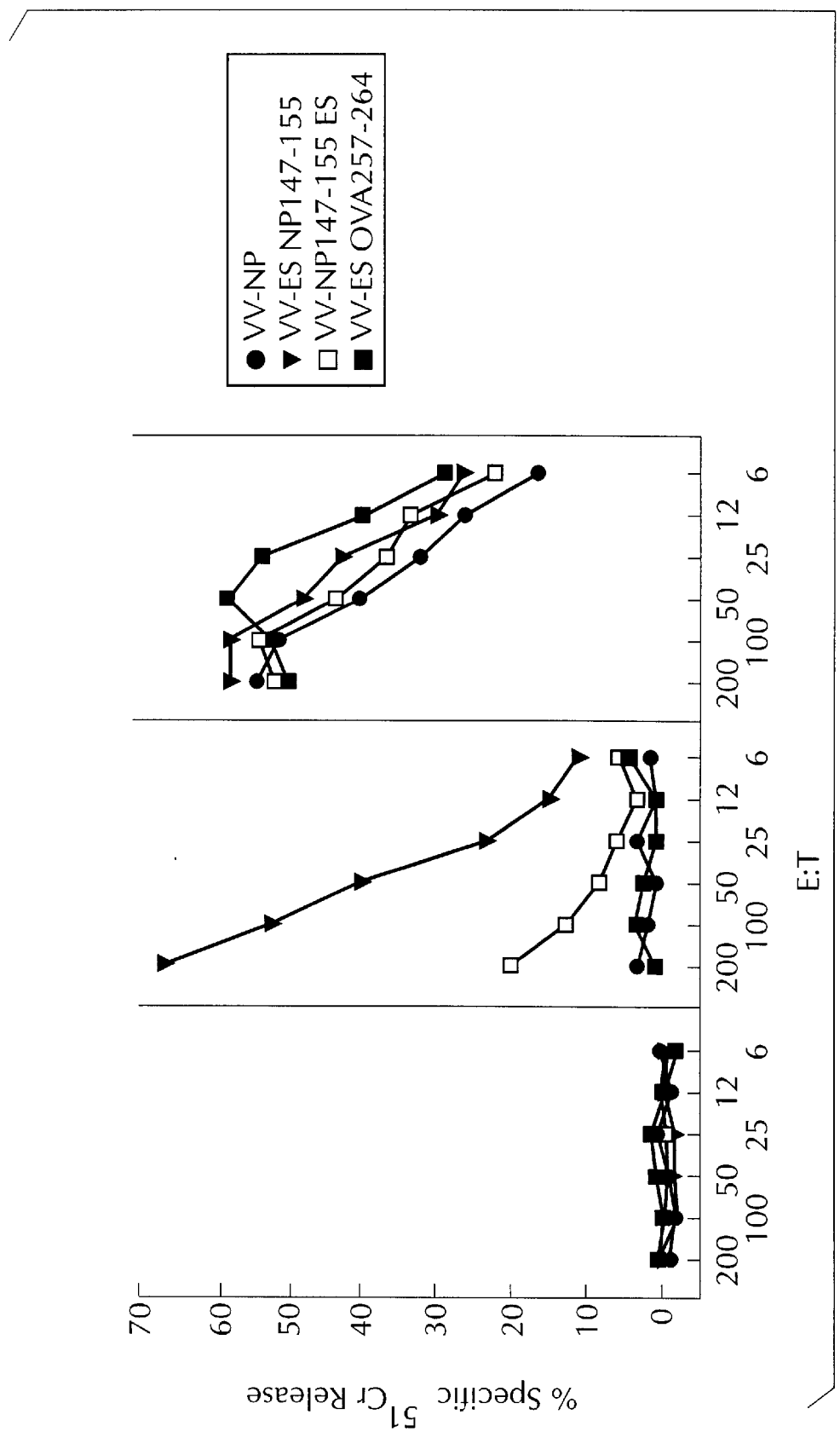
FIG. 2 shows the results of $^{51}$Cr release assays in which splenocytes derived from mice immunized with various vaccinia viruses (right-hand side of figure) were incubated at different effector:target (E:T) ratios with P815 target cells (left panel), P815 cells pulsed with the synthetic peptide NP147–155 (middle panel) or P815 cells infected with wild-type vaccinia virus (VV) (right panel).
Figure 5:
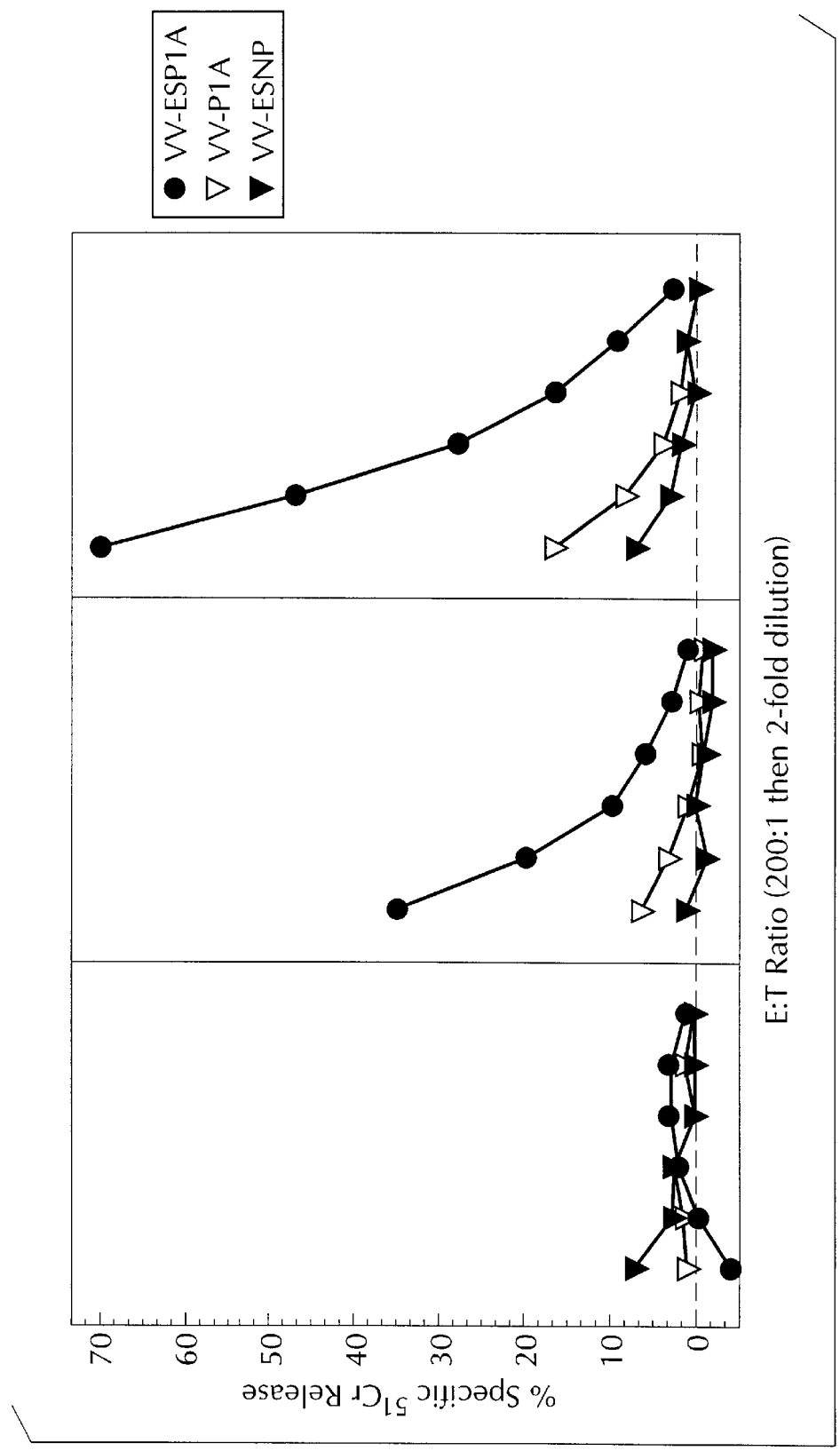
FIG. 5 shows the results of $^{51}$Cr release assays in which splenocytes derived from mice immunized with vaccinia virus VV-ESP1A (closed circles), VV-P1A (open triangles) or VV-ESNP (closed triangles) were incubated at various effector:target (E:T) ratios with CT26 target cells (left panel), CT26 cells pulsed with P1A peptide (middle panel) or P815 cells (right panel).
Figure 6:
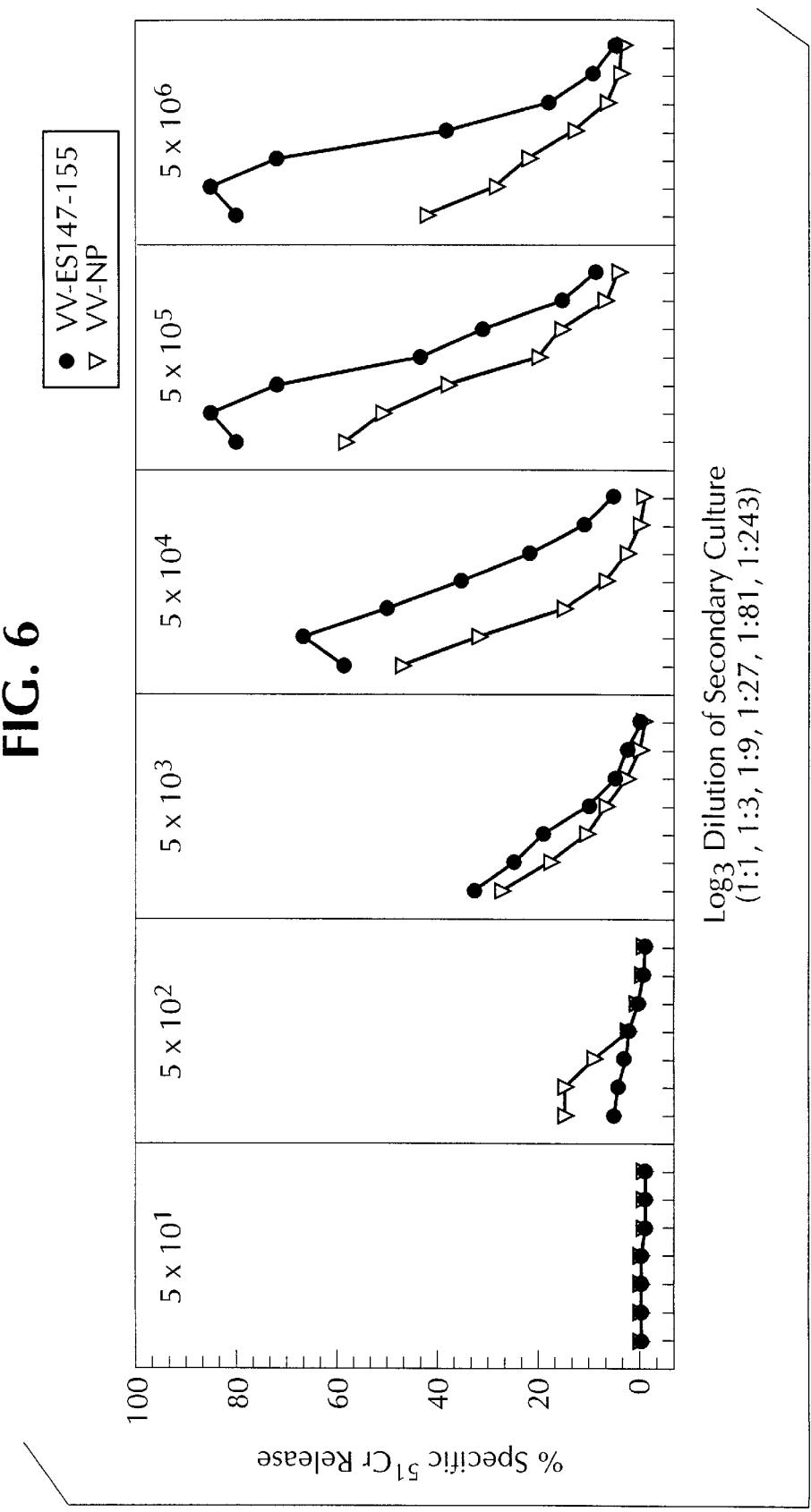
FIG. 6 shows the results of $^{51}$Cr release assays in which splenocytes derived from mice immunized with the recombinant vaccinia virus VV-ESNP 147–155 (closed circles) or VV-NP (open triangles) were subsequently cocultured with autologous cells (Restifo, N. P. et al. J. of Immunol. 47:1453–1459 (1991)) infected with influenza virus prior to incubating these splenocytes at the indicated dilutions with P815 target cells pulsed with the synthetic peptide NP 147–155.

To test whether antigen presentation of a tumor peptide might be enhanced in a manner similar to that observed for viral peptide NP 147–155 in FIG. 2, $5\times10^6$ pfu of either VV-ESP1A, VV-P1A or VV-ESNP were administered to mice. Six days following intravenous injection, spleens were harvested and splenocytes were cultured with P1A peptide via intravenous injection for six days and then were tested in a $^{51}$Cr-release assay for cytotoxicity against CT26 tumor cells (left panel), CT26 cells pulsed with P1A peptide (middle panel) or P815 cells (right panel). The source of the effector splenocytes is indicated at the bottom of FIG. 5 and the $^{51}$Cr-release assay was conducted at an effector to target ratio of 200:1 followed by serial two-fold dilutions. As expected, all three VV constructs tested failed to elicit a CD8+ T cell response against the CT26 target cells (left panel). In addition, splenoctyes derived from mice immunized with VV-ESP1A demonstrated much greater P1A-specific activity than that observed for splenocytes derived from mice immunized with VV-P1A (middle versus right panels). These results suggest that the use of ER chimeric proteins comprising an ER signal sequence amino terminal to an immunogenic peptide may be of general utility in enhancing the antigen presentation of that peptide processed via interaction with class I MHC molecules.

EXAMPLE 6

Secondary NP-Specific Response of Splenocytes Derived From Mice Immunized With Either VV-ES NP147–155 or VV-NP To determine if the "ES" construct (VV-ES NP147–155) primed more efficiently for secondary responses of CD8+ T cells than did VV-NP, mice were immunized with either VV-ES NP 147–155 (circles) or VV-NP (triangles) at the following dosages (in pfu): $5 \times 10^1$, $5 \times 10^2$, $5 \times 10^3$, $5 \times 10^4$, $5 \times 10^5$, $5 \times 10^6$. Mice were then allowed to generate a "memory" response for thirty days, at which time, mice were sacrificed and splenocytes were removed and stimulated in vitro for 7 days with influenza virus. The secondarily-stimulated splenocyte populations were then assayed at various dilutions (from left to right in each panel: 1:1, 1:3, 1:9, 1:27, 1:81 and 1:243) against P815 cells pulsed with peptide NP 147–155 in a $^{51}Cr$ release assay. The results show that at the lower doses tested, there was little difference between the ability of the two VV constructs to prime for secondary NP peptide-specific responses (some priming was observed with as little as 500 pfu). However, at doses of $5 \times 10^4$ pfu or higher, priming with VV-ES NP147–155 resulted in the recovery of splenocytes approximately 10 times as active as splenocytes from VV-NP primed-mice. The results demonstrate that adding a signal sequence to the minimal antigenic determinant or peptide enhances both secondary and primary NP-specific CD8+ T cell responses.

EXAMPLE 7

Figure 7:
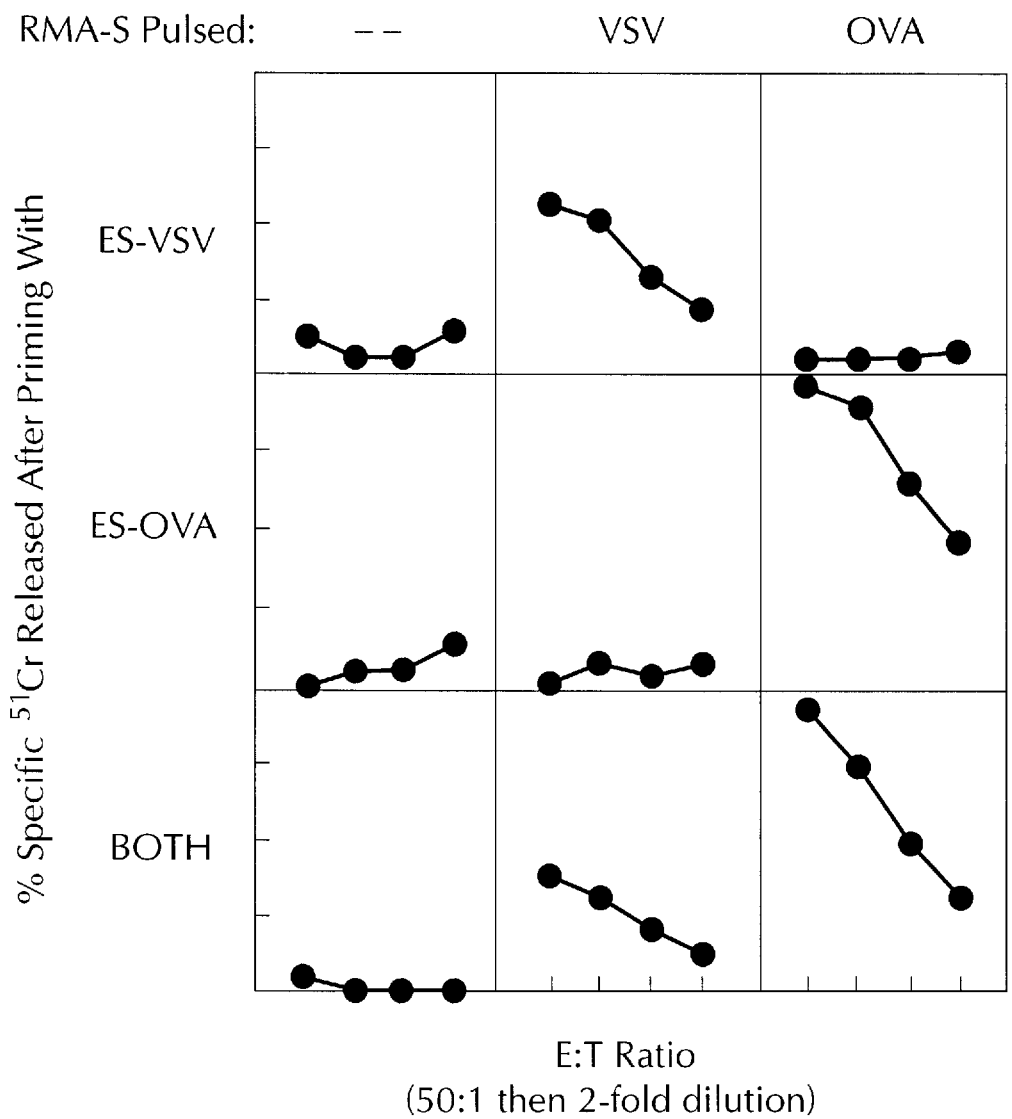
FIG. 7 shows the results of $^{51}$Cr release assays in which splenocytes derived from mice immunized with either vaccinia virus VV-ES VSV 52–59 (top row), VV-ES OVA257–264 (middle row) or both viruses mixed together (bottom row) were incubated with RMA-S target cells (left column), RMA-S cells pulsed with peptide VSV 52–59 (middle column) or RMA-S cells pulsed with peptide OVA 257–264 (right column).

Administration of More Than One Recombinant Vaccinia Virus Construct in a Single Dose Elicits a T Cell Response Specific to Each Construct In order to determine whether two different vaccinia virus constructs could elicit a CD8+ cell response when administered simultaneously, mice were intravenously injected with $2 \times 10^6$ pfu of VV-ES VSV52–59 alone (tap panels), $5 \times 10^6$ pfu of VV-ES OVA257–264 alone (middle panels) or $2 \times 10^6$ pfu of each construct together (bottom panels) and their spleen cells were isolated. Six days following immunization, mice were sacrificed wand their spleens were harvested. The splenocytes were then assayed in a $^{51}Cr$ release assay (FIG. 7) for their ability to lyse control RMA-S cells (left columns), RMA-S cells pulsed with peptide VSV52–59 (middle column) or RMA-S cells pulsed with peptide OVA257–264 (right columns).

The assays were conducted using a 50:1 E:T ratio (right hand most point in each panel) followed by succeeding 2-fold dilutions (i.e. 100:1, 200:1 etc.). As expected, none of the splenocytes tested lysed control RMA-s cells (left panels) while splenocytes derived from mice immunized with VV-ES OVA257–264 specifically lysed RNA-s cells pulsed with peptide OVA257–264 (middle row, right panel) and splenocytes derived from mice immunized with VV-ES VSV52–59 specifically lysed RNA-S cells pulsed with peptide VSV52–59 (top row, center panel). In addition, splenocytes derived from mice immunized with both VV-ES OVA257–264 and VV-ES VSV52–59 demonstrated both VSV-specific lysis (bottom row, center panel) and OVA-specific lysis (bottom row, right panel) at levels comparable to those observed for splenocytes derived from mice immunized with either VV-ES VSV52–59 (top row, center panel) or VV-ESOVA 257–264 (middle row, right panel). Thus, these results demonstrated that more than one vaccinia virus construct could be administered together without any loss in their ability to stimulate specific CD8+ T cell responses to each construct.

EXAMPLE 8

Vaccine Against Infection by P815 Tumor Cells

Immunogenic chimeric proteins or vaccinia virus constructs encoding immunogenic chimeric proteins may be used to prevent cancer, infectious disease or autoimmune disease in both humans and animals. For example, female DBA/2 mice are given intravenously $10^4$–$10^8$ pfu of vaccinia virus VV-ES P1A or 0.1 ug to 1.0 mg of the corresponding ER chimeric peptide. Three days to six months following immunization (to allow for generation of an immune response), mice are challenged intravenously or intraperitoneally or subcutaneously with $10^2$ to $10^6$ P815 tumor cells. Mice are then monitored for tumor development starting immediately following administration of the P815 challenge dose either by measurement of subcutaneous tumor or by mouse death or by monitoring the mice for lung and/or liver and/or spleen metastases by visual and microscopic inspection.

EXAMPLE 9

Method Of Treatment For Mammals Having Tumor P815

Immunogenic chimeric proteins or vaccinia virus constructs encoding immunogenic chimeric proteins may be efficacious in treating mammals having cancer, infectious disease or autoimmune disease. For example, female DBA-2 mice are given $10^2$–$10^6$ P815 tumor cells intravenously, intraperitoneally or subcutaneously. After one to twenty-one days have elapsed in order to allow the tumor to establish itself, the mice are given $10^4$ to $10^8$ pfu of vaccinia virus VV-ES P1A or 0.1 ug to 1.0 mg of the corresponding ER chimeric protein. The mice are then monitored for a decrease in tumor size or for disappearance of the tumor altogether either by mouse death or by monitoring lung and/or liver and/or spleen metastases by visual or microscopic inspection.

EXAMPLE 10

Treatment of Mammals Having P815 Tumor by Adoptive Immunotherapy $10^4$–$10^8$ pfu of vaccinia virus VV-ESP1A or 0.1 ug to 0.1 mg of the corresponding immunogenic chimeric protein is given intravenously to female DBA/2 mice. From about 3 days to six months following immunization (to allow for generation of an immune response), the spleen or tumor of the mouse is harvested and the lymphocytes contained within the spleen or tumor are isolated using dounce homogenizers. These lymphocytes are then administered at $10^7$–$10^{11}$ cells intravenously or intraperitoneally to a mouse having a P815 induced tumor. Treatment can occur one to 21 days following induction of a P815 tumor in mice by administering $10^2$–$10^6$ P815 tumor cells to mice intravenously, intraperitoneally or subcutaneously. The treated mice are then monitored for a decrease in tumor size or for disappearance of the tumor altogether by either mouse death or by monitoring lung and/or liver and/or spleen metastases by visual or microscopic inspection.

As will be apparent to those skilled in the art in the light of the foregoing disclosure, many modifications, alterations and substitutions are possible in the practices of this invention without departing from the spirit or scope thereof.

We claim:

1. A DNA construct which directs host organism synthesis of an immunogenic chimeric protein, said DNA construct having a nucleic acid sequence comprising:
    (a) a first sequence encoding an endoplasmic reticulum signal sequence peptide; and
    (b) a second sequence encoding at least one other peptide selected from the group consisting of tumor peptides, bacterial peptides, parasitic peptides and autoimmune disease peptides, where said other peptide forms a complex with class I MHC molecules.

2. The DNA construct of claim 1, wherein said first sequence encodes an endoplasmic reticulum signal sequence peptide having an amino acid sequence according to SEQ ID NO:1.

3. The DNA construct of claim 1, wherein said second sequence encodes a tumor peptide.

4. The DNA construct of claim 1, wherein said second sequence encodes a bacterial peptide.

5. The DNA construct of claim 1, wherein said second sequence encodes a parasitic peptide.

6. The DNA construct of claim 1, wherein said second sequence encodes an autoimmune disease peptide.

7. A eukaryotic cell transfected with the DNA construct of claim 1.

8. A method of producing a T cell response in a mammal comprising administering the DNA construct of claim 1 to said mammal in an amount effective to elicit said T cell response.

9. A eukaryotic cell transfected with the DNA construct of claim 2.

10. A method of producing a T cell response in a mammal comprising administering the DNA construct of claim 2 to said mammal in an amount effective to elicit said T cell response.

11. The DNA construct of claim 3, wherein the tumor peptide has an amino acid sequence according to SEQ ID NO:6.

12. A eukaryotic cell transfected with the DNA construct of claim 3.

13. A method of producing a T cell response in a mammal comprising administering the DNA construct of claim 3 to said mammal in an amount effective to elicit said T cell response.

14. A eukaryotic cell transfected with the DNA construct of claim 4.

15. A method of producing a T cell response in a mammal comprising administering the DNA construct of claim 4 to said mammal in an amount effective to elicit said T cell response.

16. A eukaryotic cell transfected with the DNA construct of claim 5.

17. A method of producing a T cell response in a mammal comprising administering the DNA construct of claim 5 to said mammal in an amount effective to elicit said T cell response.

18. A eukaryotic cell transfected with the DNA construct of claim 6.

19. A method of producing a T cell response in a mammal comprising administering the DNA construct of claim 6 to said mammal in an amount effective to elicit said T cell response.

20. A eukaryotic cell transfected with the DNA construct of claim 11.

21. A method of producing a T cell response in a mammal comprising administering the DNA construct of claim 11 to said mammal in an amount effective to elicit said T cell response.

22. A DNA construct which directs host organism synthesis of an immunogenic chimeric protein, said DNA construct having a nucleic acid sequence comprising:
   (a) a first sequence encoding an endoplasmic reticulum signal sequence peptide; and
   (b) a second sequence encoding at least one viral peptide selected from the group consisting of an adenovirus EIA peptide, an SV40 T antigen peptide, an Epstein Barr virus peptide, and a vesicular stomatitis virus peptide.

23. A eukaryotic cell transfected with the DNA construct of claim 22.

24. A method of producing a T cell response in a mammal comprising administering the DNA construct of claim 22 to said mammal in an amount effective to elicit said T cell response.

* * * * *